United States Patent [19]

Scher

[11] 4,314,841

[45] Feb. 9, 1982

[54] BENZYL THIOCARBAMATE SULFOXIDES STABILIZED WITH CALCIUM CARBONATE CARRIER

[75] Inventor: Herbert B. Scher, Moraga, Calif.

[73] Assignee: Stauffer Chemical Company, Westport, Conn.

[21] Appl. No.: 235,216

[22] Filed: Feb. 17, 1981

Related U.S. Application Data

[63] Continuation of Ser. No. 96,952, Nov. 23, 1979, abandoned, which is a continuation-in-part of Ser. No. 23,864, Mar. 26, 1979, abandoned.

[51] Int. Cl.³ .............................................. A01N 25/22
[52] U.S. Cl. .......................................... 71/88; 71/103; 71/94; 71/95; 71/DIG. 1
[58] Field of Search .................... 71/88, 103, DIG. 1, 71/94, 95

[56] References Cited

U.S. PATENT DOCUMENTS 3,785,798  1/1974  Horai ..................................... 71/79
3,897,492  7/1975  Tilles ............................. 260/551 R
4,008,071  2/1977  Gozzo ................................... 71/99

Primary Examiner—Catherine L. Mills
Attorney, Agent, or Firm—M. Henry Heines

[57] ABSTRACT

The thermal instability and carrier deactivation of a herbicidal benzyl thiocarbamate sulfoxide is reduced by use of a calcium carbonate carrier.

28 Claims, No Drawings

BENZYL THIOCARBAMATE SULFOXIDES STABILIZED WITH CALCIUM CARBONATE CARRIER

CROSS REFERENCE TO RELATED APPLICATIONS

This is a continuation of application Ser. No. 096,952, filed Nov. 23, 1979 now abandoned which is a continuation-in-part of Application Ser. No. 023,864, filed Mar. 26, 1979 now abandoned.

This invention relates to stabilized granular benzyl thiocarbamate sulfoxide compositions and to a method of reducing thermal instability and carrier deactivation of herbicidal benzyl thiocarbamate sulfoxides.

BACKGROUND OF THE INVENTION AND PRIOR ART

Benzyl thiocarbamate sulfoxides are well known in the pesticide art for their excellent herbicidal activity. A full description of such compounds together with their preparation and method of use is found in U.S. Pat. No. 3,897,492.

Unfortunately, thiocarbamate sulfoxides tend to decompose. This has been found to occur while the compounds are placed in storage for extended periods of time, and tends to accelerate at elevated temperatures. In addition, contact with dry soil and even with the clay and mineral carriers used in common pesticide formulations has been found to induce decomposition and deactivation of the compounds. A study on the stability of these compounds is found in Gozzo et al., "On the Thermal and Chemical Stability of Carbamoyl Sulfoxides," *The Journal of Chemistry and Industry*, Mar. 1, 1975.

The literature reports various attempts to stabilize thiocarbamate sulfoxides by adding stabilizing agents: the use of crystalline carbamoyl sulfoxide/urea adducts is described in U.S. Pat. No. 4,008,071, the use of hindered phenols is described in U.S. Pat. No. 4,117,010, and the use of acetylenic compounds is described in U.S. Pat. No. 4,081,468.

It has now been discovered that improved stability can be achieved in a granular benzyl thiocarbamate sulfoxide composition without the use of added stabilizing agents.

DESCRIPTION OF THE INVENTION

The present invention resides in a novel granular composition comprising a benzyl thiocarbamate sulfoxide and calcium carbonate. Calcium carbonate functions as a carrier in the present composition, and has the unexpected advantage of prolonging the stability of the benzyl thiocarbamate sulfoxide to a considerably greater extent than conventional clay carrier materials.

Specifically, the present invention resides in a granular herbicidal composition comprising (a) from 0.5% to 50% by weight, preferably from 1% to 25% by weight, of a benzyl thiocarbamate sulfoxide of the formula

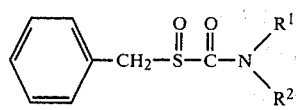

in which $R^1$ and $R^2$ are independently selected from the group consisting of $C_1$–$C_6$ alkyl, $C_2$–$C_6$ alkenyl, and $C_2$–$C_6$ alkynyl, or $R^1$ and $R^2$ conjointly form $C_3$–$C_{10}$ alkylene; and (b) from 50% to 99.5% by weight, preferably from 75% to 95% by weight, calcium carbonate.

This invention also resides in a method of controlling undesirable vegetation which comprises applying to the locus where control is desired an herbicidally effective amount of the above granular composition.

Also included within the scope of this invention is soil treated with an herbicidally effective amount of the above granular composition.

In the benzyl thiocarbamate sulfoxide formula shown above, certain embodiments are preferred, namely those in which $R^1$ and $R^2$ are independently $C_1$–$C_6$ alkyl or conjointly from $C_4$–$C_6$ alkylene.

The terms "alkyl," "alkenyl," "alkynyl," and "alkylene" are intended to include both straight-chain and branched-chain groups. The term "alkylene" is used herein to denote a bivalent saturated hydrocarbon radical. Examples include such groups as $-CH_2CH_2CH_2CH_2-$, $-CH_2CH_2CH_2CH_2CH_2-$, $-CH_2CH_2CH_2CH_2CH_2CH_2-$, and $-CH_2CH(CH_3)CH_2CH_2CH_2-$. All carbon atom ranges are intended to be inclusive of their upper and lower limits.

Examples of S-benzyl thiocarbamate sulfoxides within the scope of the present invention include S-benzyl methyl-s-butynylthiocarbamate sulfoxide, S-benzyl ethylisobutylthiocarbamate sulfoxide, S-benzyl dipropylthiocarbamate sulfoxide, S-benzyl propylbutylthiocarbamate sulfoxide, S-benzyl diethylthiocarbamate sulfoxide, S-benzyl dibutylthiocarbamate sulfoxide, S-benzyl butylisobutylthiocarbamate sulfoxide, S-benzyl butyl-s-butylthiocarbamate sulfoxide, S-benzyl isobutyl-s-butylthiocarbamate sulfoxide, S-benzyl ethylbutylthiocarbamate sulfoxide, S-benzyl ethyl-s-butylthiocarbamate sulfoxide, S-benzyl ethyl-t-butylthiocarbamate sulfoxide, S-benzyl propylisobutylthiocarbamate sulfoxide, S-benzyl dimethylthiocarbamate sulfoxide, S-benzyl ethylpentylthiocarbamate sulfoxide, S-benzyl ethyl-s-pentylthiocarbamate sulfoxide, S-benzyl methyl 1,3-dimethylbutylthiocarbamate sulfoxide, S-benzyl ethylallylthiocarbamate sulfoxide, S-benzyl 1-tetramethyleneimine carbothiolate sulfoxide, S-benzyl 1-pentamethyleneimine carbothiolate sulfoxide, and S-benzyl 1-hexamethyleneimine carbothiolate sulfoxide.

These and other S-benzyl thiocarbamate sulfoxide herbicides within the scope of the present invention include both liquids and solids. The carrier has a limited absorptivity, however, and as a result, relatively small quantities of herbicide are preferred when a liquid herbicide is used. Thus, with liquid herbicides, a quantity ranging from 1% to 5% by weight of the granule is preferred.

The granular compositions of the present invention can be prepared either by impregnating calcium carbonate chips with the herbicide or by mixing calcium carbonate powder and the herbicide into an aqueous paste from which water is subsequently removed. The latter process is generally preferred since it allows the manufacturer to control the properties of the finished granule by modifying the agglomeration and drying processes. In addition, one can obtain granules with a higher proportion of herbicide when a paste is used. When granules are formed in this manner, however, a binder is included in the composition to maintain the integrity of the granule. The binder will comprise from 0.5% to 20%, preferably from 1% to 10% by weight of the composition.

The term "binder" is used herein to denote any film-forming agent capable of agglomerating a carrier material into a granule. In the pesticide art, a variety of materials are commonly known as binders, and all such materials are useful in the present invention. In general, binders fall into two categories—polymers and swelling clays.

Polymeric binders include both water-soluble and water-dispersible types. Examples of water-soluble polymeric binders are polyvinyl alcohol, polyacrylamide, polyvinylpyrrolidone, polyethylene oxide, carboxymethylcellulose, sodium alginate, and sodium lignin sulfonate. Examples of water-dispersible polymeric binders are polyvinylacetate, poly(vinylacetate-acrylate), poly(vinylacetate-maleate), poly(styrene-butadiene), poly(styrene-acrylate), and poly(vinylacetate-butyrate).

The swelling clay binders are chiefly montmorillonite- and bentonite-type clays. The most common examples are sodium montmorillonite and sodium bentonite.

Like the conventional carriers, some binders also adversely affect the stability of the thiocarbamate sulfoxide herbicide. Preferred binders, therefore, are those which are relatively inert. In general, polymeric binders are more inert than swelling clays, and are likewise preferred.

The following examples illustrate the composition of the present invention and its properties in contrast to those of similar compositions. These examples are merely illustrative and are intended neither to define nor limit the invention in any manner.

TEST 1

This test was conducted to determine stability of benzyl thiocarbamate sulfoxides on calcium carbonate, calcium sulfate, and magnesium carbonate carriers. The following example describes the formulation for calcium carbonate. The other formulations were made in an identical manner by substituting calcium sulfate or magnesium carbonate for calcium carbonate.

The following were combined and blended in a beaker: 1.39 grams (g) Technical S-benzyl sec-butylethyl thiocarbamate sulfoxide (94.8%), 22.36 g calcium carbonate powder, and 1.25 g ammonium lignin sulfonate binder. In another beaker, 2.50 g Technical S-benzyl hexahydro-1H-azepine-1-carbothioate sulfoxide (95.8%), 21.25 g calcium carbonate powder, and 1.25 g ammonium lignin sulfonate binder were blended. Enough water was added to each mixture to make a paste. Each paste was pressed into the bottom of a Petri dish and dried to constant weight in a 50° C. oven. The dry cake was crushed into granules.

The initial percentage of sulfoxide in the formulated granule was compared to the sulfoxide remaining after one month of storage at 32° F. The results are reported in Table I. Calcium carbonate was found to be unique for the stabilization of benzyl thiocarbamate sulfoxides.

TABLE I

| | Benzyl Thiocarbamate Sulfoxides | | | |
| | | Thermal Stability on Various Carriers After One Month Storage Temperature = 32° F. (0° C.) | | |
| Sulfoxide | Theoretical Composition of all Granules | Calcium Carbonate | Magnesium Carbonate | Calcium Sulfate |
|---|---|---|---|---|
| S-benzyl sec-butylethyl thiocarbamate sulfoxide | 5.3 | 4.7 | 0.8 | 2.3 |
| S-benzyl hexahydro-1H-azepine-1-carbothioate sulfoxide | 9.6 | 8.5 | ~0.0 | 3.7 |

TEST 2

A mixture of 111.0 g Technical S-benzyl sec-butylethyl thiocarbamate sulfoxide (90%), 1789.0 g of calcium carbonate powder, and 100.0 g of an ammonium lignin sulfonate binder was blended with enough water to give an extrudable mixture.

The mixture was extruded using a granule extruder with 0.8 millimeter (mm) screens. In order to produce extrudate with non-sticking surfaces, steam was passed through the jacket of the extruder and air was blown at the extrudate as it emerged from the screens. The air dried the surfaces, mechanically breaking down the extrudate into rods 3–6 mm in length. The extrudate was then placed on trays and dried in an oven for 16 hours at 50° C. After drying, the granules were sieved and a 14/28 mesh fraction collected as product.

The extruded granule consisted by weight of 5% S-benzyl sec-butylethyl thiocarbamate sulfoxide, 90% calcium carbonate, and 5% binder.

S-benzyl hexahydro-1H-azepine-1-carbothioate sulfoxide was formulated in the same manner, by combining 445.0 g of Technical S-benzyl hexahydro-1H-azepine-1-carbothioate sulfoxide (90%), 3355.0 g of calcium carbonate powder, and 200.0 g of ammonium lignin sulfonate binder. The extruded granule consisted by weight of 10% sulfoxide, 85% calcium carbonate, and 5% binder.

Each formulation was then tested for thermal stability by storing for one month at low and high temperature extremes at 5° F. and 125° F. The results of this test are reported in Table II.

TABLE II

| | Benzyl Thiocarbomate Sulfoxides | | |
| | | Thermal Stability on Calcium Carbonate Carrier After One Month Storage Temperature: | |
| Sulfoxide | Theoretical Composition | 5° F. (−15° C.) | 125° F. (52° C.) |
|---|---|---|---|
| S-benzyl sec-butylethyl thiocarbamate sulfoxide | 5.0% | 5.0% | 4.4% |
| S-benzyl hexahydro-1H-azepine-1-carbothioate sulfoxide | 10.0% | 9.2% | 8.8% |

TEST III

The herbicides were formulated with the calcium carbonate carrier as in Test I. The purpose of this two-part test was to measure dry soil deactivation by comparing herbicidal effectiveness of technical and formulated benzyl thiocarbamate sulfoxides in soil watered immediately after treatment and in soil where watering was delayed.

On the day before seeding fiber flats measuring 5.25×7.25×2.50 inches (13.3×18.5×6.4 cm) were filled to a depth of 2 inches (5.08 cm) with air-dried loamy clay soil treated with 50 parts per million (ppm) each of cis-N-[(trichloromethyl)thio]-4-cyclohexane-1,2-dicarboximide, a fungicide sold as Captan ®, and an 18-18-18 fertilizer, which contains 18% by weight equivalent each of nitrogen, phosphorus pentoxide, and potassium oxide. The flats were seeded with watergrass (*Echinochloa crusgalli*), wild oat (*Avena fatua*), and foxtail (Setaria sp.)

Three flats containing each weed species were atomized with 5.4 milligrams (mg) (Test A) or 5.0 mg (Test B) of either Technical S-benzyl sec-butylethyl thiocarbamate or S-benzyl hexahydro-1H-azepine-1-carbothioate. Three flats containing each weed species were also sprinkled with granules of each sulfoxide formulated with a calcium carbonate carrier. Application rates corresponded to 2 pounds per acre (lb/A) (2.25 kilograms per hectare (k/ha)).

The flats were placed on greenhouse benches where temperature was maintained between 70°–90° F. (21.5°–32.1° C.). One group of flats was watered immediately. In the second and third groups, watering was delayed until 3 and 7 days after herbicide application.

Injury ratings were taken 29 (Test A) and 24 (Test B) days after watering. The results reported in Table III indicate that dry soil deactivation was considerably reduced when the technicals were formulated as calcium carbonate granules.

The granular compositions of the present invention are in the form of particles, typically measuring about 1 to 2 millimeters in diameter. The particles consist of a calcium carbonate matrix of macroscopic dimensions supporting the herbicide which is distributed throughout. A surfactant can be included in the matrix to aid in leaching the herbicide to the surrounding soil.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds more generally known to the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the herbicide is first mixed with powdered calcium carbonate and subsequently granulated, liquid non-ionic wetters can still be used, but it is usually preferable to incorporate at the mixing stage a solid powdered anionic wetting agent such as a calcium, amine, alkanolamine, or alkali salt of an alkyl or alkylaryl sulfonate. Such agents will comprise from about 0 to 2 weight percent of the total composition.

The granular compositions of the present invention are useful in controlling the growth of undesirable vegetation by pre-emergence or post-emergence application to the locus where control is desired, including pre-plant and post-plant soil incorporation as well as surface application.

In general, any conventional method of application can be used. The locus of application can be soil, seeds, seedlings, or the actual plants, as well as flooded fields. Soil application is preferred and can be achieved by

TABLE III

Dry Soil Testing of Benzyl Thiocarbamate Sulfoxides

% Herbicidal Injury and Delayed Watering

| Herbicide | Day of Treatment | | | 3rd Day After Treatment | | | 7th Day After Treatment | | |
|---|---|---|---|---|---|---|---|---|---|
| | WG | WO | FT | WG | WO | FT | WG | WO | FT |
| S-benzyl sec-butylethyl thiocarbamate sulfoxide | | | | TEST A | | | | | |
| 85% Technical | 90 | 60 | 30 | 0 | 0 | 0 | 0 | 0 | 0 |
| % ai Formulated 2.9 | 100 | 100 | 95 | 98 | 98 | 70 | 99 | 80 | 50 |
| S-benzyl hexahydro-1H-azepine-1-carbothioate sulfoxide | | | | | | | | | |
| 88% Technical | 80 | 0 | 0 | 0 | 0 | 0 | 0 | 0 | 0 |
| % ai Formulated 9.9 | 70 | 10 | 10 | 85 | 10 | 0 | 90 | 10 | 0 |
| S-benzyl sec-butylethyl thiocarbamate sulfoxide | | | | TEST B | | | | | |
| 85% Technical | 100 | 95 | 85 | 78 | 0 | 20 | 0 | 0 | 0 |
| % ai Formulated 2.9 | 100 | 100 | 98 | 100 | 90 | 70 | 95 | 80 | 85 |
| S-benzyl hexahydro-1H-azepine-1-carbothioate sulfoxide | | | | | | | | | |
| 88% Technical | 60 | 0 | 0 | 20 | 0 | 0 | 0 | 0 | 0 |
| % ai Formulated 1.6 | 98 | 10 | 0 | 90 | 0 | 0 | 95 | 0 | 0 |
| 9.9 | 95 | 20 | 0 | 85 | 5 | 0 | 60 | 0 | 0 | ai = active ingredient
WG = Watergrass
WO = Wild Oat
FT = Foxtail conventional ground or air application equipment. In typical application, the compositions are applied to the soil surface and then distributed below the surface to a depth of at least one-half inch by conventional means such as discing, dragging, or mixing.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount used depending on the overall cost and the desired results. It will be readily apparent to one skilled in the art that compositions exhibiting lower herbicidal activity will require a higher dosage rate for the same degree of control than more active compounds.

What is claimed is:

1. In a granular herbicidal composition comprising from 0.5% to 50% by weight of a benzyl thiocarbamate sulfoxide of the formula

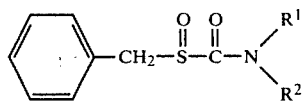

in which
R$^1$ and R$^2$ are independently selected from the group consisting of C$_1$–C$_6$ alkyl, C$_2$–C$_6$ alkenyl, and C$_2$–C$_6$ alkynyl, or
R$^1$ and R$^2$ conjointly form C$_3$–C$_{10}$ alkylene; and
from 50% to 99.5% by weight of a carrier, the improvement comprising the use of calcium carbonate as the carrier to improve the thermal stability of the benzyl thiocarbamate sulfoxide.

2. A composition according to claim 1 further comprising from 0.5% to 20% by weight of a binder.

3. A composition according to claim 2 comprising from 1% to 25% by weight of said benzyl thiocarbamate sulfoxide, from 75% to 95% by weight of calcium carbonate, and from 1% to 10% by weight of said binder.

4. A composition according to claim 2 in which R$^1$ and R$^2$ either independently are C$_1$–C$_6$ alkyl or conjointly form C$_4$–C$_6$ alkylene.

5. A composition according to claim 2 in which said binder is a water-soluble or water-dispersible polymer.

6. A composition according to claim 2 in which R$^1$ is ethyl, R$^2$ is sec-butyl, and said binder is ammonium lignin sulfonate.

7. A composition according to claim 2 in which R$^1$ and R$^2$ conjointly form hexamethylene, and said binder is ammonium lignin sulfonate.

8. In a method of controlling undesirable vegetation which comprises applying to the locus where control is desired an herbicidally effective amount of a granular composition comprising from 0.5% to 50% by weight of a benzyl thiocarbamate sulfoxide of the formula

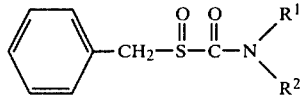

in which
R$^1$ and R$^2$ are independently selected from the group consisting of C$_1$–C$_6$ alkyl, C$_2$–C$_6$ alkenyl, and C$_2$–C$_6$ alkynyl, or
R$^1$ and R$^2$ conjointly form C$_3$–C$_{10}$ alkylene; and
from 50% to 99.5% by weight of a carrier, the improvement comprising the use of calcium carbonate as the carrier to improve the thermal stability of the benzyl thiocarbamate sulfoxide.

9. A method according to claim 8 in which said granular composition further comprises from 0.5% to 20% by weight of a binder.

10. A method according to claim 9 comprising from 1% to 25% by weight of said benzyl thiocarbamate sulfoxide, from 75% to 95% by weight of calcium carbonate, and from 1% to 10% by weight of said binder.

11. A method according to claim 9 in which R$^1$ and R$^2$ either independently are C$_1$–C$_6$ alkyl or conjointly form C$_4$–C$_6$ alkylene.

12. A method according to claim 9 in which said binder is a water-soluble or water-dispersible polymer.

13. A method according to claim 9 in which R$^1$ is ethyl, R$^2$ is sec-butyl, and said binder is ammonium lignin sulfonate.

14. A method according to claim 9 in which R$^1$ and R$^2$ conjointly form hexamethylene, and said binder is ammonium lignin sulfonate.

15. In soil treated with an herbicidally effective amount of a granular composition comprising from 0.5% to 50% by weight of a benzyl thiocarbamate sulfoxide of the formula

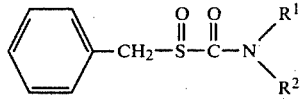

in which
R$^1$ and R$^2$ are independently selected from the group consisting of C$_1$–C$_6$ alkyl, C$_2$–C$_6$ alkenyl, and C$_2$–C$_6$ alkynyl, or
R$^1$ and R$^2$ conjointly form C$_3$–C$_{10}$ alkylene; and
from 50% to 99.5% by weight of a carrier, the improvement comprising the use of calcium carbonate as the carrier to reduce the rate of deactivation of the benzyl thiocarbamate sulfoxide when in contact with dry soil.

16. Soil treated according to claim 15 in which said granular composition further comprises from 0.5% to 20% by weight of a binder.

17. Soil treated according to claim 16 in which said granular composition comprises from 1% to 25% by weight of said benzyl thiocarbamate sulfoxide, from 75% to 95% by weight of calcium carbonate, and from 1% to 10% by weight of said binder.

18. Soil treated according to claim 16 in which R$^1$ and R$^2$ either independently are C$_1$–C$_6$ alkyl or conjointly form C$_4$–C$_6$ alkylene.

19. Soil treated according to claim 16 in which said binder is a water-soluble or water-dispersible polymer.

20. Soil treated according to claim 16 in which R$^1$ is ethyl, R$^2$ is sec-butyl, and said binder is ammonium lignin sulfonate.

21. Soil treated according to claim 16 in which R$^1$ and R$^2$ conjointly form hexamethylene, and said binder is ammonium lignin sulfonate.

22. A method of improving the thermal stability of a benzyl thiocarbamate sulfoxide of the formula

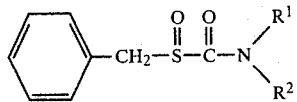

in which

R[1] and R[2] are independently selected from the group consisting of $C_1-C_6$ alkyl, $C_2-C_6$ alkenyl, and $C_2-C_6$ alkynyl, or R[1] and R[2] conjointly form $C_3-C_{10}$ alkylene, which comprises forming a granular composition comprising from 0.5% to 50% by weight of said benzyl thiocarbamate sulfoxide and from 50% to 99.5% by weight of calcium carbonate.

23. A method according to claim 22 in which said granular composition further comprises from 0.5% to 20% by weight of a binder.

24. A method according to claim 23 comprising from 1% to 25% by weight of said benzyl thiocarbamate sulfoxide, from 75% to 95% by weight of calcium carbonate, and from 1% to 10% by weight of said binder.

25. A method according to claim 23 in which R[1] and R[2] either independently are $C_1-C_6$ alkyl or conjointly form $C_4-C_6$ alkylene.

26. A method according to claim 23 in which said binder is a water-soluble or water-dispersible polymer.

27. A method according to claim 23 in which R[1] is ethyl, R[2] is sec-butyl, and said binder is ammonium lignin sulfonate.

28. A method according to claim 23 in which R[1] and R[2] conjointly form hexamethylene, and said binder is ammonium lignin sulfonate.

* * * * *